United States Patent [19]

Frass

[11] 4,101,327
[45] Jul. 18, 1978

[54] LIGHT-SENSITIVE COPYING COMPOSITIONS AND PHOTOINITIATORS CONTAINED THEREIN

[75] Inventor: Werner Frass, Naurod, Fed. Rep. of Germany

[73] Assignee: Hoechst Aktiengesellschaft, Fed. Rep. of Germany

[21] Appl. No.: 753,875

[22] Filed: Dec. 23, 1976

[30] Foreign Application Priority Data

Dec. 27, 1975 [DE] Fed. Rep. of Germany ....... 2558812

[51] Int. Cl.² .............................................. G03C 1/68
[52] U.S. Cl. ............................. 96/115 P; 96/115 R; 204/159.18; 204/159.23; 204/159.24; 548/357
[58] Field of Search ........................ 96/115 P, 115 R; 204/159.18, 159.23, 159.24

[56] References Cited

U.S. PATENT DOCUMENTS

| 3,288,608 | 11/1966 | Cautaud et al. | 96/115 R |
| 3,874,947 | 4/1975 | Hayakawa et al. | 96/115 P |
| 3,925,077 | 9/1975 | Lewis et al. | 96/115 P |
| 3,949,143 | 4/1976 | Schlesinger | 96/115 P |
| 3,959,100 | 5/1976 | McGinniss | 204/159.14 |

OTHER PUBLICATIONS

Pschorr, *Ber.* 45 (1912), pp. 2239–2251.
Jacobson, *Ber.* 43 (1910) pp. 3255–3263.
Baeyer et al., *Ann.* 393 (1912) pp. 121–124.

*Primary Examiner*—Jack P. Brammer
*Attorney, Agent, or Firm*—James E. Bryan

[57] ABSTRACT

This invention relates to a new class of photoinitiators and to copying compositions containing said photoinitiators and further comprising at least one polymeric binder and at least one ethylenicylly unsaturated polymerizable compound. The photoinitiator of the present invention is a compound of the following general Formula II:

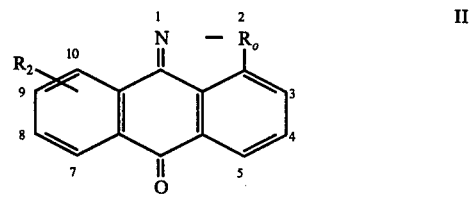

Further, this invention relates to a new class of compounds which correspond to the following general Formula I:

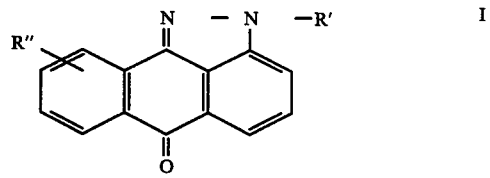

and which are particularly suitable as photoinitiator compounds coming under Formula II.

13 Claims, No Drawings

LIGHT-SENSITIVE COPYING COMPOSITIONS AND PHOTOINITIATORS CONTAINED THEREIN

The present invention relates to a new class of photoinitiators and to copying compositions prepared therewith.

Light-sensitive copying compositions, such as are presently used in the technology of reproduction, can be present in liquid form or as a solid layer on a carrier, and contain, as essential constituents, at least one binder, at least one ethylenically-unsaturated polymerizable compound and at least one photoinitiator.

Ethylenically-unsaturated polymerizable compounds are to be understood as both low-molecular weight polyfunctional monomers which are capable of addition polymerization, and poly-unsaturated high-molecular weight compounds which are capable of being photo-cross-linked.

Hydrazones, mercapto compounds, pyrylium salts or thiapyrylium salts, chalcones, dibenzal ketones, aromatic ketones or diketones, polynuclear quinones of the anthraquinone type or phenanthrenequinone type and benzanthrone and its derivatives are known photoinitiators for photopolymerization or for photo-crosslinking of unsaturated compounds.

The use of heterocyclic polynuclear compounds, such as, for example, benzthiazole and benzthiazoline derivatives, quinoxalines, quinazolines, acridines, phenazines and azabenzanthrones, as photoinitiators is also described in the literature.

A disadvantage of many of these compounds is that they are suitable only for very specific light-sensitive layers, whereas they largely lose their effectiveness in other photopolymerizable or photocrosslinkable copying compositions.

Other photoinitiators, such as, for example, the hydrazones disclosed in German Offenlegungsschrift No. 1,495,973, require the addition of suitable dyestuff sensitizers in order to increase their light-sensitivity.

Yet other photoinitiators, for example polynuclear quinones, effect only a relatively low degree of cross-linking during photopolymerization, so that image areas and non-image areas can be differentiated only when relatively large amounts of initiator are employed.

In other cases, the solubility of the photoinitiators in the solvents used for the preparation of the coating solutions is low or a number of photoinitiators are not sufficiently compatible with the materials which are additionally present in the coating solutions, such as, for example, binders and/or monomers, dyestuffs, plasticizers and the like.

Inadequate compatibility is frequently also observed in the copying compositions themselves, in particular when they are subjected to relatively large temperature fluctuations under unfavorable storage conditions. This results in the photoinitiator exuding and/or crystallizing out, which entails a decrease of the light-sensitivity, sometimes leads to a substantial deterioration of adhesion and very adversely affects the storability of the copying composition.

It is the object of the invention to provide a new class of photoinitiators which do not possess the above-mentioned defects and which, in particular, make it possible, within wide limits, to vary the solubility of the compounds and their compatibility with various substrates by simple manipulations, on the molecule, which do not affect the groupings responsible for the initiator activity of the molecule.

According to the invention, compounds of the general formula I

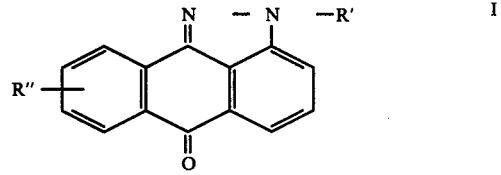

wherein R' is an alkyl group with 1 – 6 carbon atoms, which is substituted by hydroxyl, alkoxy, alkoxycarbonyl or acyl, an aralkyl group with 7 – 10 carbon atoms, an alkylcarbonyl group with 3 – 18 carbon atoms, or an arylsulfonyl group, and R'' is hydrogen, an alkoxy group, or halogen, are employed.

It now has been found that known compounds, the molecular structure of which is related to that of the new photoinitiators, also are effective as photoinitiators.

According to the invention, a light-sensitive copying composition therefore is also provided which, as essential constituents, contains at least one polymeric binder, at least one ethylenically-unsaturated polymerizable compound and, as the photoinitiator, at least one polynuclear heterocyclic nitrogen compound of the general formula II

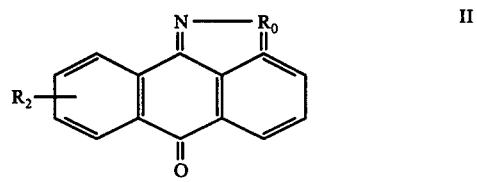

wherein $R_o$ is O, S, or $NR_1$ and $R_1$ is hydrogen, a saturated or unsaturated unsubstituted alkyl group with 1 – 6 carbon atoms, a saturated or unsaturated alkyl group with 1 – 6 carbon atoms which is substituted by hydroxyl, alkoxy, alkoxycarbonyl, acyl, acyloxy and/or halogen, an aralkyl group with 7 – 10 carbon atoms, an acyl group with 2 – 18 carbon atoms or a polyalkyleneoxide group of the general formulae $-(C_aH_{2a}-O)_n-C_aH_{2a}-OH$ or $-(C_aH_{2a}-O)_n-C_aH_{2a}-OCH_3$ wherein $a = 2$ to 4 and $n = 1$ to 10, and $R_2$ is hydrogen, an alkoxy group, an alkyl group with 1 – 6 carbon atoms or halogen.

The new compounds according to the invention, which can carry the most diverse substituents on a heterocyclic base structure, are distinguished by good solubility, a low tendency to crystallize in highly viscous photopolymeric copying compositions, and good compatibility in layers of the most diverse composition.

The new photoinitiators of the type of 6-oxo-anthra-(1,9-cd)-2-(6H)-pyrazole, corresponding to formula I, can readily be prepared from the base compound ($R_1 =$ H) by reaction with the corresponding epoxides in dimethylformamide or by reaction with acid chlorides in pyridine. The compounds have a light yellow to dark red color and their absorption maximum is within the range of 360 μ – 450 μ.

As examples of specific representatives, corresponding to the general formula I, of the type of 6-oxo-anthra-(1,9-cd)-2-(6H)-pyrazoles, the following compounds are illustrative which are substituted by R' and R'' and in which R' is an alkyl group with 1 – 6, preferably 2 – 4, carbon atoms, which is substituted by hydroxyl, alkoxy, alkoxycarbonyl or acyl, the numbers 1 - 6 indicating the number of carbon atoms arranged as a straight chain in the substituted alkyl group. R' also can be an aralkyl group with 7 - 10 carbon atoms, preferably benzyl or toluyl, and an alkylcarbonyl group (= alkanoyl group) and 3 = 18 carbon atoms, for example propionyl to stearyl, or an arylsulfonyl group, preferably benzene-sulfonyl or tosyl. R" can be in the 7-, 8-, 9- or 10-position, preferably in the 10-position, and can be hydrogen, an alkoxy group, preferably methoxy or ethoxy, or halogen, preferably chlorine or bromine.

The photoinitiators which can be used in the light-sensitive copying composition proposed according to the invention, are derived from the formula II, described initially, in which the substituent $R_o$ is O, S or $NR_1$, and $R_1$ represents hydrogen, a lower unsubstituted alkyl group with 1 - 6, preferably 2 - 4, carbon atoms and also an alkyl group with 1 - 6, preferably 2 - 4, carbon atoms, which is substituted by hydroxyl, alkoxy, alkoxycarbonyl, acyl or halogen, preferably chlorine or bromine, the numbers 1 to 6 indicating the number of carbon atoms arranged as a straight chain in the substituted alkyl group.

$R_1$ also can be the allyl group, an aralkyl group with 7 - 10 carbon atoms, preferably benzyl or toluyl, and an acyl group with 2 - 18 carbon atoms, preferably acetyl to stearyl, benzoyl, methoxybenzoyl, ethoxybenzoyl, methylbenzoyl, benzene-sulfonyl or tosyl.

The substituent $R_2$ can be in the 7-, 8-, 9- or 10-position, preferably in the 10-position, and can be hydrogen, an alkyl group with 1 - 6 carbon atoms, preferably methyl or ethyl, an alkoxy group, preferably methoxy or ethoxy, or halogen, preferably chlorine or bromine.

Table I is a selection of suitable photoinitiators of the type claimed according to the invention, corresponding to formula II.

The item numbers of the compounds from this table are utilized in the examples given for characterizing the particular photoinitiators used.

Further suitable photoinitiators are the compounds which are listed below and are likewise derived from the formula II ($R_o = NR_1$), wherein

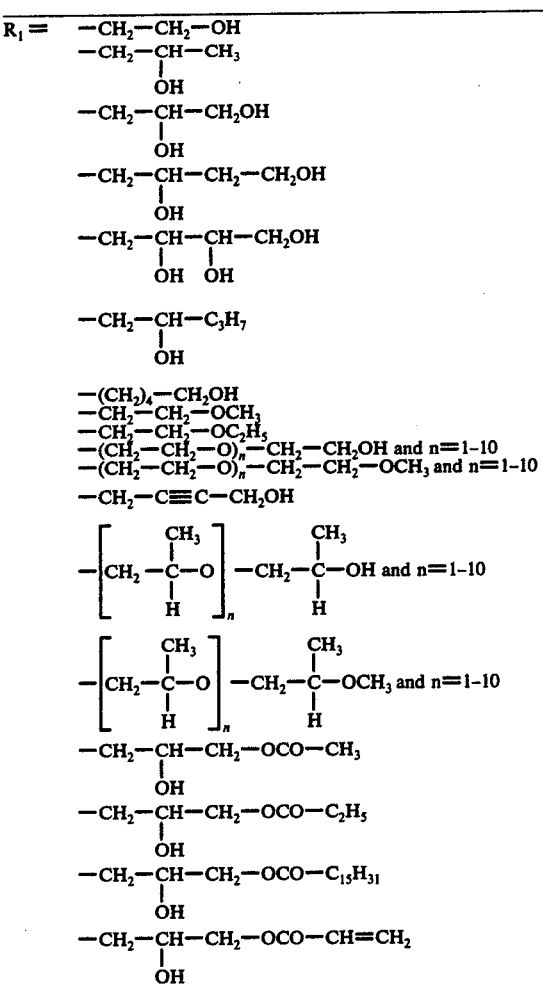

TABLE I

| No. | $R_1$ | $R_2$ | Melting Point | N found | N calc. | S found | S calc. |
|---|---|---|---|---|---|---|---|
| 1 | Allyl | H | 110–112° | 10.3 | 10.8 | | |
| 2 | n-$C_4H_9$ | H | 148–149° | 9.8 | 10.1 | | |
| 2 | i-$C_4H_9$ | H | 151–153° | 9.7 | 10.1 | | |
| 4 | Benzyl | H | 183–185° | 8.7 | 9.0 | | |
| 5 | $CH_2COOC_2H_5$ | H | 206–208° | 8.7 | 9.1 | | |
| 6 | $CH_2CO-C_6H_5$ | H | 220–221° | 8.2 | 8.3 | | |
| 7 | $CH_2CH(OH)C_2H_5$ | H | 146° | 9.3 | 9.6 | | |
| 8 | $COCH_3$ | H | 213° | | | | |
| 9 | $COC_2H_5$ | H | 172–173° | 10.0 | 10.1 | | |
| 10 | $COC_3H_7$ | H | 157–158° | 9.7 | 9.7 | | |
| 11 | $COC_7H_{15}$ | H | 105–106° | 7.8 | 8.1 | | |
| 12 | $COC_6H_5$ | H | 225–228° | 8.8 | 8.6 | | |
| 13 | $CO-C_6H_4p(OCH_3)$ | H | 229–230° | 8.0 | 7.9 | | |
| 14 | $SO_2-C_6H_4p(CH_3)$ | H | 184–186° | 7.1 | 7.5 | 7.5 | 8.5 |
| 15 | Benzyl | $OC_2H_5$ | 204–206° | 7.7 | 7.9 | | |
| 16 | $CH_2COOC_2H_5$ | $OC_2H_5$ | 211–212° | 8.0 | 8.0 | | |
| 17 | $CH_2-CO-C_6H_5$ | $OC_2H_5$ | 189–190° | 8.3 | 7.3 | | |
| 18 | $CH_2CH(OH)C_2H_5$ | $OC_2H_5$ | 160–162° | 8.1 | 8.3 | | |
| 19 | $COCH_3$ | $OC_2H_5$ | 253–256° | 8.8 | 9.1 | | |
| 20 | $COC_2H_5$ | $OC_2H_5$ | 229–231° | 8.5 | 8.7 | | |
| 21 | $COC_3H_7$ | $OC_2H_5$ | 222–223° | 8.1 | 8.4 | | |
| 22 | $COC_7H_{15}$ | $OC_2H_5$ | 165–166° | 7.1 | 7.4 | | |
| 23 | $COC_6H_5$ | $OC_2H_5$ | 134–136° | 7.0 | 7.6 | | |
| 24 | $COC_6H_4p(OCH_3)$ | $OC_2H_5$ | 229–231° | 7.1 | 7.0 | | |
| 25 | $CH_2CH(OH)C_2H_5$ | | 153–154° | 8.6 | 8.6 | | |
| 26 | $CH_2CH(OH)CH_2Cl$ | Cl | 165–167° | 8.0 | 8.1 | | |
| 27 | $COCH_3$ | Cl | | | | | |
| 28 | $R_o = O$ | H | | | | | |
| 29 | $R_o = S$ | H | | | | | |

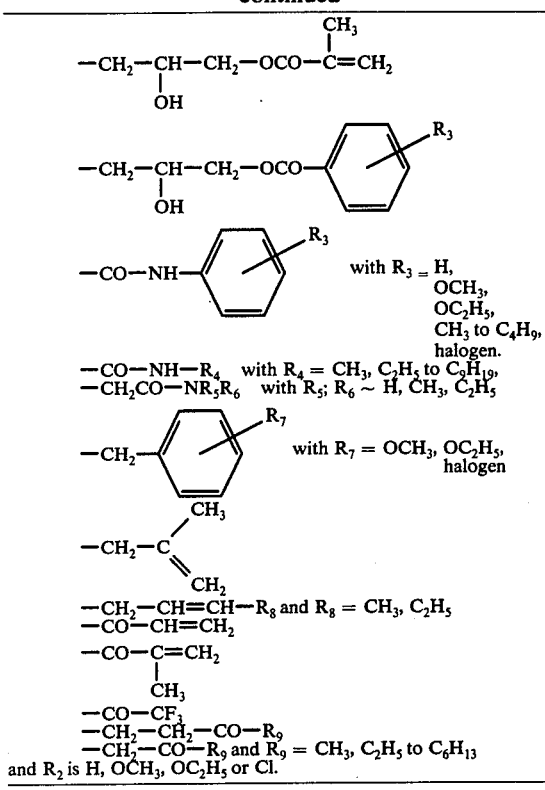

The copying compositions according to the invention contain, as essential constituents, binders, liquid and/or solid polymerizable organic compounds and photoinitiators of the type described above.

Examples of suitable monomers are commercially available acrylic acid esters and methacrylic acid esters, inter alia, those of diethylene glycol, triethylene glycol, tetraethylene glycol and polyethylene glycol, of trimethylolethane and trimethylolpropane, diglycerol diacrylate, guaiacol glycerol ether diacrylate, neopentyl glycol diacrylate, 2,2-dimethylolbutan-3-ol diacrylate, unsaturated esters of pentaerythritol, as described in U.S. Pat. No. 3,261,686, reaction products of trimethylolpropane, alkylene oxide and acrylic acids or methacrylic acids according to U.S. Pat. No. 3,380,831, and acrylates or methacrylates of polyesters containing hydroxyl groups. The latter and further monomers which are suitable for use in the photopolymer layers according to the invention are described, for example, in U.S. Pat. Nos. 2,760,863, and 3,060,023. The monomers which are known from DT-OS 2,064,079, and contain urethane groups, and the monomers which are known from DT-OS 2,361,041, and contain the biuret group

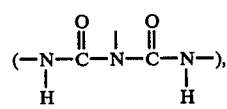

can be used in the same way.

As this list shows, the invention is not restricted to the use of any specific polymerizable monomer; it is advantageous that the monomer is at least ethylenically diunsaturated and is capable of addition polymerization. If poly-unsaturated high-molecular weight compounds are used, these must either be themselves susceptible to photocrosslinking or must be susceptible to addition polymerization together with a low-molecular weight monomer. The unsaturated compounds listed below are, for example, suitable for use in light-sensitive copying compositions:

Polyvinyl cinnamates and prepolymers of unsaturated esters, for example the prepolymer of diallyl isophthalate, or the polymeric allylimides disclosed in DT-OS No. 2,203,732, and polyvinylacetals with extralinear vinylidene groups, corresponding to U.S. Pat. No. 2,902,710.

If commercially available monomers, or advantageously monomers prepared on site, are employed, these normally contain small amounts (about 50 – 100 ppm) of an inhibitor in order to prevent a thermally induced polymerization.

If the copying compositions according to the invention are intended to withstand extreme storage conditions without change, the amount of inhibitor added can be increased to 1% by weight, relative to the monomer used.

Inter alia, the following compounds are suitable as thermal inhibitors:

p-Methoxyphenol, hydroquinone, alkyl-substituted and aralkylsubstituted quinones and hydroquinones, tert.-butyl-catechol, pyrogallol, copper resinate, naphthylamines, $\beta$-naphthol, copper-I chloride, 2,6-di-tert.-butyl-p-cresol, phenothiazine, pyridine, nitrobenzene and dinitrobenzene, p-toluquinone, chloranil and thiazine dyestuffs, such as, for example, thionine Blue G.

The photopolymerizable copying compositions also can contain, in a known manner, one or more binders which are soluble in solvents, for example polyamides, polyvinyl acetates, polymethyl(meth)-acrylates, polyvinyl butyrals, cellulose ethers or cellulose esters, polyalkylene ethers and condensation polymers of glycols with dibasic acids, or binders which are soluble or can be swollen or softened in alkali, for example styrene/maleic anhydride copolymers, copolymers of ethylene and maleic anhydride or of alkyl methacrylate and methacrylic acid, corresponding to DT-OS No. 2,064,080, terpolymers of styrene, alkyl methacrylate and methacrylic acid, corresponding to DT-OS No. 2,363,806, copolymers of methyl methacrylate and N-(p-toluenesulfonyl)-carbamic acid ($\beta$-methacryloxy)-ethyl ester, corresponding to DT-OS No. 2,027,466, maleate resins, terpene-phenolic resins and the like.

Since development frequently is carried out with aqueous-alkaline developers, those binders are preferably used which are soluble in alkali or can be softened in aqueous alkalies. Examples of such binders are copolymers of styrene with maleic anhydride and of alkyl methacrylate with methacrylic acid, terpolymers of styrene, alkyl methacrylate and methacrylic acid, maleate resins and the copolymers disclosed in DT-OS No. 2,205,146.

Plasticizers, adhesion promoters, hydrogen donors, oxygen scavengers, dyestuffs, pigments, color couplers, UV absorbers and sensitometric regulators also can be added to the copying compositions.

The nature and quantity of these additives depend upon the field of application intended for the copying composition according to the invention. Additionally, care should be taken that the substances added do not absorb an excessive proportion of the actinic light required for the initiation process and thus diminish the actual light-sensitivity.

Inter alia, suitable plasticizers are dibutyl phthalate, diisooctyl adipate, nitrate esters, alkyl phosphate and aryl phosphate esters, chlorinated paraffins, glycols or aliphatic polyols. If perfect storability at high atmospheric humidity is to be ensured, water-insoluble plasticizers are preferably used.

Adhesion promoters are employed whenever the light-sensitive copying compositions are to be subjected to special stresses, such as, for example, when they are used as photoresist materials. Monomeric or polymeric organic silanes, nitrogen-containing heterocyclic compounds, such as are disclosed, for example, in U.S. Pat. Nos. 3,645,722, 3,622,234 and 3,827,908, heterocyclic mercaptans according to DT-OS No. 2,028,773, and mercaptoalkanoic acid anilides corresponding to DT-OS No. 2,448,821, or mercaptoalkanoic acid esters according to DT-OS No. 2,448,750, have been found suitable as adhesion promoters.

Examples of hydrogen donors to be used, in known manner, are substances with aliphatic ether bonds or cyclic $\beta$-dicarbonyl compounds. If appropriate, this function also can be fulfilled by the binder or the polymerizable substance if these possess a labile hydrogen atom.

The photopolymerizable copying compositions also can contain dyestuffs and/or pigments, which can act both as contrast agents and as layer consolidators. Examples of dyestuffs which can be used are disclosed in U.S. Pat. Nos. 3,218,167, and 3,884,693.

Furthermore, the copying compositions according to the invention can contain UV absorbers which act as antihalo filters. Examples of suitable non-coloring compounds are disclosed in DT-OS No. 2,243,182.

Within the scope of the invention, the following distribution by weight of the most important constituents is preferred in the light-sensitive copying composition, the percentages indicated denoting percent by weight, relative to the total solids content: binder 15 – 98.4%, monomers 1 – 75%, photoinitiator 0.1 – 10%, hydrogen donor 0.5 – 10%, plasticizer 0 – 15%, adhesion promoter 0 – 15%, and dyestuff or pigment 0 – 30%.

The light-sensitive copying compositions according to the invention can be commercially utilized in the form of a solution or dispersion for example as a so-called photoresist, which is applied by the consumer himself to an individual carrier, as is customary, for example, for chemical milling, for the manufacture of copied circuits or stencils, labelings, screen printing forms and the like, and are exposed after drying and developed imagewise. In this case, the constituents of the light-sensitive copying composition are dissolved in a suitable solvent. Alcohols, ketones, esters, ethers, amides, hydrocarbons and the like are suitable as solvents. The partial ethers of glycols or of keto-alcohols have proved to be advantageous solvents; however, the selection of the solvent depends largely on the selection of the binder.

In particular, however, the light-sensitive copying composition according to the invention also can be marketed in the form of a solid photopolymerizable layer, present on a carrier material, for the manufacture of printing forms, relief images, etch resists, stencils, matrices, screen printing forms, individual copies and the like. Storable, presensitized printing plates for planographic printing, letterpress printing and gravure printing represent a particularly important application.

Coating of the carrier material is carried out from appropriate organic solvents or solvent mixtures, namely by casting, spraying or dipping.

Examples of suitable layer carriers are magnesium, zinc; copper; mechanically, chemically and electrochemically roughened aluminum; anodized aluminum, and steel, but also polyester film or acetate film, Perlon gauze and the like, the surface of which can have been subjected to a pretreatment, if required. The carrier material here can act as the final carrier or as an intermediate carrier material from which the light-sensitive copying composition is transferred by lamination to the workpiece to be processed. For the preparation of thick photopolymer layers, the thickness of which can amount to several tenths of a millimeter, the copying composition according to the invention also can be kneaded, without dissolution in a solvent, for example in a three-roll mill, the hydraulically pressed onto the carrier sheet, for example under 30,000 to 50,000 kp for one minute at 90° C.

If crosslinking is effected solely by the polymerization of the ethylenically-unsaturated monomers, it is in general advantageous to seal off the light-sensitive copying compositions according to the invention against atmospheric oxygen during exposure because oxygen very easily captures and deactivates the radicals forming in the layer. Such a seal is effected in a simple manner by a barrier layer which is impermeable to oxygen, such as is disclosed, for example, in German Offenlegungsschriften Nos. 1,572,153, and 2,036,585.

In the case where a high-molecular weight compound susceptible to a photochemical crosslinking reaction is used in the light-sensitive copying composition and the crosslinking is not effected exclusively or predominantly by low-molecular weight acrylates or alkyl acrylates, such a barrier layer is not necessary because this photocrosslinking leads to the desired differentiation between the exposed and the unexposed areas even in the presence of oxygen.

The recording material manufactured with the light-sensitive copying compositions serves, on the one hand, for the preparation of images on suitable carriers or receiving sheets and, on the other hand, for the preparation of reliefs which are used as printing forms, screens, resists and the like. Furthermore, however, it is also possible to use the light-sensitive copying compositions for formulating UV-curing lacquers which can be employed as surface protection or for formulating UV-curing printing inks which neither dry physically nor crosslink chemically with an oxygen-induced formation of transverse bonds. Drying takes place photochemically and is thus particularly fast and does not pollute the environment.

The printing forms, screens, resists and the like are prepared from suitable recording materials in the manner customary in the trade, i.e., after exposure under a suitable original, the non-image areas which have remained soluble are removed by treatment with suitable solvents, for example aqueous-alkaline solutions.

Development, however, also can be accomplished by other methods, namely by utilizing other physical differences, known in the trade, between cured image areas and uncured non-image areas, for example differences in melting point, in tackiness, in adhesion, in optical transparency and the like.

The invention will be further illustrated by the following examples.

Unless otherwise stated, all quantity data are to be understood as relating to weight.

The designations parts by weight and parts by volume bear the same relationship to one another as g/ml.

EXAMPLE 1

The compounds, according to the invention, of the formula I can by synthesized in accordance with one of the preparation instructions indicated as follows:

Instruction A 2.5 parts by weight of 6-oxo-anthra-(1,9-cd)-2-(6H)-pyrazole (formula I, R' = H; R" = H) are suspended in 25.0 parts by volume of dimethylformamide, while stirring. 0.3 part by weight of $K_2CO_3$ is added to this suspension, whereupon the 6-oxo-anthra-(1,9-cd)-2-(6H)-pyrazole goes into solution giving a red color. The solution is warmed to 70°, a solution of 1.2 parts by weight of 1-butene oxide in 5.0 parts by volume of dimethyl formamide is added dropwise and the reaction mixture is maintained at 100° C for four hours; the dark brown solution is then allowed to cool and poured into 120.0 parts of volume of $H_2O$/ice.

The solid product precipitated is filtered off and recrystallized.

Yield: 1.9 parts by weight = 58% of theoretical.
Melting point: 146° C (from xylene).
$N_{calculated}$ 9.55%, $N_{found}$ 9.3%.

Instruction B 12.0 parts by weight of 6-oxo-anthra-(1,9-cd)-2-(6H)-pyrazole are dissolved in 480.0 parts by volume of pyridine, while stirring. 7.8 parts by weight of freshly distilled propionyl chloride are then added dropwise in the course of 10 minutes, the temperature rising by about 2° - 3° C. After about 20 minutes, a precipitate begins to settle out. The reaction mixture is left to stand for three hours and is then poured into 1,500.0 parts by volume of ice water, a yellow precipitate settling out.

The precipitate is filtered off and recrystallized.
Yield: 11 parts by weight.
Melting point: 172° - 173° C (from chlorobenzene).
$N_{calculated}$ 10.15%, $N_{found}$ 10.0%.

In detail, the compounds Nos. 4, 5, 6, 7, 15, 16, 17, 18, 25 and 26 were prepared in accordance with Instruction A and the compounds Nos. 9, 10, 11, 14, 20, 21 and 22 were prepared in accordance with Instruction B, using the corresponding starting materials.

The Instructions A and B similarly can be applied to the preparation of the compounds listed on pages 6 to 8.

EXAMPLE 2

140.0 parts by weight of a copolymer of methyl methacrylate and methacrylic acid, having an average molecular weight of 35,000 and an acid number of 86, 140.0 parts by weight of trimethylolethane triacrylate and 1.5 parts by weight of tri-[4-(3-methyl-phenylamino)-phenyl]-methyl acetate are dissolved in 1,400.00 parts by weight of ethylene glycol monoethyl ether.

In each case, 0.05 part by weight of a photoinitiator listed in Table II, page 18, is added to 16.8 parts by weight of the solution. The solution is stirred until the solid has dissolved, then filtered, and whirler-coated, on a disc whirler at 100 rpm, onto aluminum foils the surface of which had been subjected to an electrochemical roughening treatment. The dried layer is coated with a covering layer composed of 2.0 parts by weight of carboxymethyl cellulose, 1.0 part by weight of saccharose, 1.0 part by weight of saponin and 0.12 part by weight of sorbic acid in 267.0 parts by weight of water, dried, and exposed in each case for two minutes in a vacuum copying frame under a 21-step halftone wedge from Eastman Kodak Co. (Kodak, Photographic Tablet No. 2), the wedge having a density range of 0.05 - 3.05 with density increments of 0.15. The light source used is a 8,000 W Xenokop point-source lamp at a distance of 72 cm.

In order to remove the non-image areas, the plates are then wiped over for 30 seconds with a developer composed of 15 parts by weight of sodium metasilicate nonahydrate, 3 parts by weight of polyethylene glycol 6,000, 0.6 part by weight of levulinic acid and 0.3 part by weight of strontium hydroxide octahydrate in 1,000 parts by weight of water and having a pH of 11.9, and then rinsed with water.

If the copying layers are processed as described above, the photoinitiator effect of the substance under investigation can be determined from the number of fully reproduced steps of the halftone wedge. For this, the general rule applies: the larger the number of wedge steps, the higher the light-sensitivity in practice.

Table II summarizes the results for the compounds tested in accordance with the instructions indicated above: columns 3 and 4 contain, respectively, the number of fully reproduced wedge steps or the number of the wedge steps which are still just recognizable. The light-sensitivities of two adjacent wedge steps differ by the factor $\sqrt{2}$. The wedge step 0 corresponds to the optical density 0.05 (individual absorption of the film material).

TABLE II

| Compound | Experiment No. | Wedge Steps fully reproduced | still recognizable |
|---|---|---|---|
| 1 | 1 | 1 | 4 |
| 2 | 2 | 0 | 2 |
| 3 | 3 | 0 | 2 |
| 5 | 4 | 1 | 3 |
| 7 | 5 | 1 | 5 |
| 9 | 6 | 1 | 6 |
| 10 | 7 | 1 | 4 |
| 11 | 8 | 1 | 5 |
| 14 | 9 | 1 | 5 |
| 25 | 10 | 1 | 4 |
| 26 | 11 | 1 | 4 |

EXAMPLE 3

A solution of 36 parts by weight of diallyl isophthalate prepolymer and 9 parts by weight of pentaerythritol triacrylate in 290 parts by weight of 2-methyl-2-methoxy-pentan-4-one is prepared.

In each case, 0.16 part by weight of a photoinitiator listed in Table III is added to 33.5 parts by weight of this solution and the latter is stirred until complete dissolution has occurred.

The solutions are then filtered and applied to mechanically roughened aluminum foil on a disc whirler at 100 rpm. After adequate drying (15 minutes at 50° C) the light-sensitive layers are exposed under a 21-step halftone grey wedge (Kodak, Photographic Step Tablet No. 2) in a vacuum copying frame by means of a 8,000 W xenon point-source lamp from a distance of 72 cm. After exposure, the samples are bathed for 60 seconds in 1,1,1-trichloroethane in order to remove the non-image areas, and then sprayed with pure solvent.

Then each plate is treated for 45 seconds, using a plush plug, with an etching solution disclosed in DT-OS No. 1,940,280, and composed of 12.0 parts by volume of phosphoric acid (85%), 80.0 parts by volume of gum arabic (14° Be), 0.2 part by volume of hydrofluoric acid (50%), 0.5 part by volume of hydrogen peroxide (30%) and 7.3 parts by volume of water.

The plates are then inked with greasy ink. The relative light-sensitivities can be seen from the comparison of the wedge steps listed in the following table.

TABLE III

| Compound | Experiment No. | Wedge Steps fully reproduced | still recognizable |
|---|---|---|---|
| 1 | 12 | 8 | 10 |
| 2 | 13 | 3 | 7 |
| 3 | 14 | 3 | 6 |
| 4 | 15 | 8 | 10 |
| 5 | 16 | 7 | 8 |
| 6 | 17 | 7 | 10 |
| 7 | 18 | 5 | 7 |
| 8 | 19 | 14 | 17 |
| 9 | 20 | 8 | 11 |
| 10 | 21 | 8 | 10 |
| 11 | 22 | 5 | 8 |
| 12 | 23 | 7 | 9 |
| 13 | 24 | 2 | 6 |
| 14 | 25 | 6 | 9 |
| 15 | 26 | 0 | 3 |
| 16 | 27 | 2 | 5 |
| 17 | 28 | 2 | 6 |
| 18 | 29 | 3 | 5 |
| 19 | 30 | 9 | 12 |
| 20 | 31 | 3 | 7 |
| 21 | 32 | 9 | 13 |
| 22 | 33 | 2 | 6 |
| 23 | 34 | 1 | 3 |
| 24 | 35 | 1 | 3 |
| 25 | 36 | 4 | 8 |
| 26 | 37 | 5 | 8 |
| 27 | 38 | 6 | 10 |
| 29 | 39 | 4 | 7 |

EXAMPLE 4

Three solutions are prepared each containing 140.0 parts by weight of a copolymer which is composed of methyl methacrylate and methacrylic acid, has an average molecular weight of 35,000 and an acid number of 86, 140.0 parts by weight of pentaerythritol triacrylate and 1.5 parts by weight of tri-[4-(3-methyl-phenylamino)-phenyl]-methyl acetate in 1,400.0 parts by weight of ethylene glycol monoethyl ether.

7.0 parts by weight of compounds 1, 4, or 9 are added to each one of these solutions.

The solutions are whirler-coated, by means of a disc-whirler, onto electrochemically roughened aluminum foils and are, as described in Example 1, coated with a covering layer, exposed and developed. The experimental results are evaluated in a manner corresponding to Example 1. Table IV contains the data obtained.

TABLE IV

| Compound | Experiment No. | Wedge Steps fully reproduced | still recognizable |
|---|---|---|---|
| 1 | 40 | 1 | 7 |
| 4 | 41 | 3 | 8 |
| 9 | 42 | 1 | 6 |

EXAMPLE 5

Five solutions are prepared each containing 140.0 parts by weight of a copolymer which is composed of methyl methacrylate and methacrylic acid and has an average molecular weight of 43,000 and an acid number of 86, 140.0 parts by weight of trimethylolethane triacrylate and 1.5 parts by weight of a blue azo dyestuff obtained by coupling 2,4-dinitro-6-chloroben-zenediazonium salt with 2-methoxy-5-acetylamino-N-cyano-ethyl-N-hydroxyethylaniline, in 1,400.0 parts by weight of ethylene glycol monoethyl ether.

5.0 parts by weight of compounds 6, 7, 9, 17, or 28 are added to each one of these solutions and the latter are stirred until the solid constituents have dissolved.

The solutions are filtered and whirler-coated, on a disc-whirler (100 rpm), onto electrochemically roughened and anodized aluminum foil.

The light-sensitive layers are then coated with a solution of 3.5 parts by weight of polyvinyl alcohol, 1.0 part by weight of sodium lauryl-ether-sulfate and 96.5 parts by weight of water, and dried. The further processing is carried out corresponding to that of Example 1.

Table V gives the experimental results.

TABLE V

| Compound | Experiment No. | Wedge Steps fully reproduced | still recognizable |
|---|---|---|---|
| 6 | 43 | 4 | 7 |
| 7 | 44 | 1 | 3 |
| 9 | 45 | 5 | 6 |
| 17 | 46 | 0 | 2 |
| 28 | 47 | 1 | 3 |

EXAMPLE 6

Five solutions are prepared containing 4.0 parts by weight of a reaction product from a 1 : 1 ethylene-/maleic anhydride copolymer and allylamine, corresponding to Example 9 of DT-OS 2,203,732, 1.0 part by weight of pentaerythritol triacrylate and 0.09 part by weight of one of the photoinitiators listed below, in 57.5 parts by weight of methyl ethyl ketone.

The photoinitiators used are the compounds 5, 8, 19, and 27 and, for comparison, Michler's ketone which is known as a photoinitiator.

The solutions are filtered, applied, with the aid of a disc-whirler, to mechanically roughened aluminum foil and dried.

After exposure under a halftone wedge (Kodak, Photographic Step Tablet No. 2) in a 8,000 W xenon point-source copying frame (distance 72 cm) for 2 minutes, the samples are developed by dipping in methyl ethyl ketone for one minute. They are then rinsed with water and further treated, as described in Example 2.

The relative light-sensitivities can be seen from a comparison of the wedge steps listed in Table VI.

TABLE VI

| Compound | Experiment No. | Wedge Steps fully reproduced | still recognizable |
|---|---|---|---|
| 5 | 48 | 4 | 8 |
| 8 | 49 | 4 | 7 |
| 19 | 50 | 5 | 7 |
| 27 | 51 | 5 | 8 |
| Michler's ketone | 52 | 2 | 6 |

Michler's ketone, used for comparison, shows a starter activity substantially lower than that of the oxo-anthrapyrazoles tested at the same time.

It will be obvious to those skilled in the art that many modifications may be made within the scope of the present invention without departing from the spirit thereof, and the invention includes all such modifications.

What is claimed:

1. A light-sensitive copying composition which contains about 15 to 98.4% by weight of at least one polymeric binder, about 1 to 75% by weight of at least one ethylenically-unsaturated polymerizable compound, and about 0.1 to 10% by weight of at least one polynuclear heterocyclic nitrogen compound as a photoinitiator having the general formula II

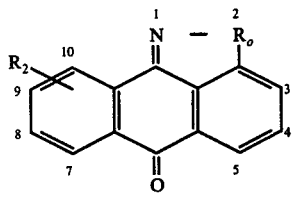

wherein $R_o$ is O, S, or $NR_1$ and $R_1$ is hydrogen, a saturated or unsaturated unsubstituted alkyl group with 1 – 6 carbon atoms, a saturated or unsaturated alkyl group with 1 – 6 carbon atoms which is substituted by hydroxyl, alkoxy, alkoxycarbonyl, acyl, acyloxy and/or halogen, an aralkyl group with 7 – 10 carbon atoms, an acyl group with 2 – 18 carbon atoms or a polyalkyleneoxide group of the general formulae $-(C_a-H_{2a}-O)_n-C_a-H_{2a}-OH$ or $-(C_aH_{2a}-O)_n-C_aH_{2a}-OCH_3$ wherein $a = 2$ to 4 and $n = 1$ to 10, and $R_2$ is hydrogen, an alkoxy group, an alkyl group with 1 – 6 carbon atoms or halogen.

2. A copying composition according to claim 1 in which $R_1$ is the acyl radical of an aliphatic carboxylic acid with 2 – 18 carbon atoms.

3. A copying composition according to claim 1 in which $R_1$ is an arylsulfonyl group with 6 to 8 carbon atoms.

4. A copying composition according to claim 1 in which $R_1$ is an alkyl group with 1 – 6 carbon atoms, which is substituted by a hydroxyl group.

5. A copying composition according to claim 1 wherein $R_1$ is an alkyl group with 2 to 4 carbon atoms, which is substituted by hydroxy, alkoxy, alkoxycarbonyl or acyl, a benzyl, toluyl, benzenesulfonyl or toluenesulfonyl group.

6. A copying composition according to claim 1 wherein $R_2$ is in the 10 position of formula II.

7. A copying composition according to claim 1 wherein $R_2$ is H, methoxy, ethoxy, Cl, or Br.

8. A copying composition according to claim 1 wherein the ethylenically-unsaturated polymerizable compound contains at least two additional polymerizable ethylenically-unsaturated groups.

9. A copying composition according to claim 1 further including a polymerization inhibitor.

10. A copying composition according to claim 1 wherein the polymeric binder is soluble or swellable in aqueous-alkaline solutions.

11. A copying composition according to claim 1 comprising about 15 – 98.4% by weight of binder, 1 – 75% by weight of ethylenically-unsaturated compound, 0.1 – 10% by weight of said polynuclear heterocyclic nitrogen compound, 0.5 – 10% by weight of a hydrogen donor, 0 – 15% by weight of a plasticizer, 0 – 15% by weight of an adhesion promoter, and 0 – 30% by weight of a dyestuff or a pigment, based on the total solids content.

12. A copying composition according to claim 1 in the form of a light-sensitive layer on a carrier.

13. A copying composition according to claim 1 in the form of a solution in a solvent.

* * * * *